(12) United States Patent
Wimberger-Friedl et al.

(10) Patent No.: US 7,558,446 B2
(45) Date of Patent: Jul. 7, 2009

(54) ALL POLYMER OPTICAL WAVEGUIDE SENSOR

(75) Inventors: Reinhold Wimberger-Friedl, Veldhoven (NL); Gert 'T Hooft, Eindhoven (NL); Christiane De Witz, Lommel (BE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/089,939

(22) PCT Filed: Oct. 10, 2006

(86) PCT No.: PCT/IB2006/053710

§ 371 (c)(1),
(2), (4) Date: Apr. 11, 2008

(87) PCT Pub. No.: WO2007/043005

PCT Pub. Date: Apr. 19, 2007

(65) Prior Publication Data

US 2008/0219616 A1  Sep. 11, 2008

(30) Foreign Application Priority Data

Oct. 12, 2005  (EP) ................. 05109455

(51) Int. Cl.
*G02B 6/00* (2006.01)
(52) U.S. Cl. ....................................... 385/12
(58) Field of Classification Search .............. 385/12, 385/13
See application file for complete search history.

(56) References Cited

U.S. PATENT DOCUMENTS 5,093,888 A * 3/1992 Takezawa et al. ........... 385/141

(Continued)

FOREIGN PATENT DOCUMENTS

JP  2001166166 A  6/2001

(Continued)

OTHER PUBLICATIONS

Dubendorfer et al: "Compact Integrated Optical Immunosensor Using Replicated Chirped Grating Coupler Sensor Chips"; Applied Optics, vol. 37, No. 10, Apr. 1998, pp. 1890-1894.

(Continued)

*Primary Examiner*—Charlie Peng (57) ABSTRACT

The present invention is directed to an evanescent field induced optical sensor of a transparent polymer substrate coated with a thin transparent polymer waveguide for use as biosensor for detecting biological molecules, wherein the transparent polymer waveguide has a thickness of $\geq 0.10$ μm and $\leq 0.50$ μm and a refractive index $n_D$ of 1.39 to 1.79, said transparent polymer waveguide has a coupling grating recess structure for enhancing the coupling of the light wave into said transparent polymer waveguide, the lower surface of said transparent polymer waveguide contacts the transparent polymer substrate, said transparent polymer substrate has a refractive index n of 1.29 to 1.69, wherein the material of said transparent polymer waveguide and said transparent polymer substrate is selected such that the difference of the refractive index $\Delta n_D$ of said transparent polymer waveguide and said transparent polymer substrate is at least $\Delta$ n 0.1, the outer upper surface of said polymer waveguide possess specific binding compounds to detect at least one specific chemical and/or biochemical substance or the outer upper surface of said polymer waveguide is covered with a thin noble metal layer.

21 Claims, 5 Drawing Sheets

U.S. PATENT DOCUMENTS

| | | | |
|---|---|---|---|
| 6,728,429 B1 * | 4/2004 | Melman et al. | 385/12 |
| 7,212,693 B2 * | 5/2007 | Carr et al. | 385/12 |
| 2001/0041025 A1 | 11/2001 | Farahi | |
| 2002/0110839 A1 | 8/2002 | Bach et al. | |
| 2005/0094958 A1 | 5/2005 | Dorn et al. | |

FOREIGN PATENT DOCUMENTS

| | | | |
|---|---|---|---|
| WO | WO9533197 A1 | 12/1995 | |
| WO | WO9821571 A1 | 5/1998 | |
| WO | WO0235214 A1 | 5/2002 | |
| WO | WO2005015173 A1 | 2/2005 | |

OTHER PUBLICATIONS

Ramsden J.: "Optical Biosensors"; Journal of Molecular Recognition, vol. 10, May 1997, pp. 109-120.

* cited by examiner

ALL POLYMER OPTICAL WAVEGUIDE SENSOR

FIELD OF THE INVENTION

This invention relates to an all-polymer optical waveguide sensor. More specifically, the invention relates to a method of manufacture and an evanescent field induced optical sensor of a transparent polymer substrate and a thin transparent polymer waveguide for use as a chemical or biosensor of detecting biological molecules. The invention also relates to the use of said sensor in qualitative affinity sensing and to the use thereof for the selective quantitative determination of luminescent components in solutions.

BACKGROUND OF THE INVENTION

Evanescent luminescence excitation is of great interest in the analytical field, as the excitation is limited to the direct environment of the wave-guiding layer. In particular, Evanescent field excited fluorescence is a very important technology for biosensors because of its unique sensitivity.

A waveguide biosensor consists generally in the simplest case of a 3-layer system, a first substrate, an inorganic wave-conducting layer, and a second substrate comprising the sample for assaying. An example of a waveguide biosensor having an inorganic wave-conducting layer is disclosed in WO 95/33197. Waveguide biosensor with an inorganic wave-conducting layer on an inorganic substrate suffers in that the waveguide biosensor has an insufficient flexibility and high manufacturing cost. Further, bending and/or warming of a waveguide biosensor with an inorganic wave-conducting layer on an organic substrate, which is more time and thus cost effective to produce, often leads to a delamination of the polymeric substrate attached to the inorganic wave-conducting layer. Thus, there is the need to provide a waveguide biosensor having a high flexibility, high delamination resistance as well as a low vertical range of manufacture.

Methods and apparatus for detecting the evanescently excited luminescence of antibodies or antigens labelled with luminescent dyes are known and described, inter alia, in US-A1-2002/0110839. The arrangement claimed therein uses a system of a reaction matrix comprising a waveguide capable of guiding and channeling light and having on the surface of said waveguide a cladding layer having at least one area of depletion in form of nanowells wherein a substance placed within said depletion area can be illuminated by the evanescent wave of light channeled in said waveguide. The manufacture of a nanowells micro array-cladding layer requires a more complex and more accurate process. The quite small nanowells requires a more accurate and still more complex positioning of the bound molecules in all the wells, which leads to a further drawback.

Therefore, it is one object of the present invention to provide an optical waveguide sensor for use as a chemical or biosensor of detecting biological molecules, which can be easily produced, does not need a high precision, has a high flexibility, high delamination resistance and a low vertical range of manufacture so that said sensors can be used as disposable articles in view of low manufacture and material cost and has at the same time a sufficient high demand of the optical and detection quality of said sensor.

SUMMARY OF THE INVENTION

This object is achieved in providing an evanescent field induced optical sensor of a transparent polymer substrate coated with a thin transparent polymer waveguide for use as biosensor for detecting biological molecules, wherein the transparent polymer waveguide has a refractive index n of 1.39 to 1.79, said transparent polymer waveguide has a coupling grating recess structure for enhancing the coupling of the light wave into said transparent polymer waveguide, the lower surface of said transparent polymer waveguide contacts a transparent polymer substrate, said transparent polymer substrate has a refractive index n of 1.29 to 1.69 and the outer upper surface of said polymer waveguide or optical sensor possess specific binding compounds to detect at least one specific chemical and/or biochemical substance or the outer upper surface of said polymer waveguide is covered with a thin noble metal layer.

It can be preferred, that said optical sensor of a transparent polymer substrate coated with a thin transparent polymer waveguide for use as biosensor for detecting biological molecules, has a transparent polymer waveguide with a thickness of $\geq 0.10\,\mu m$ and $\leq 0.50\,\mu m$ and a refractive index n of 1.39 to 1.79, said transparent polymer waveguide has a coupling grating recess structure for enhancing the coupling of the light wave into said transparent polymer waveguide, the lower surface of said transparent polymer waveguide contacts a transparent polymer substrate, said transparent polymer substrate has a refractive index n of 1.29 to 1.69, wherein the material of said transparent polymer waveguide and said transparent polymer substrate is selected such that the difference of the refractive index $\Delta n$ of said transparent polymer waveguide and said transparent polymer substrate is at least $\Delta n\ 0.1$ In its simplest form the optical sensor consists of a transparent polymeric substrate with a low refractive index and a thin layer of a high refractive index transparent polymeric waveguide spin-coated on top of the upper surface of said transparent polymeric substrate, wherein the outer upper surface of said polymer waveguide possess specific binding compounds to detect at least one specific chemical and/or biochemical substance.

Preferably the optical sensor is an all polymer sensor.

More preferred, the transparent polymer of the polymer waveguide and the transparent polymer substrate are transparent organic polymers.

In order to achieve a sufficient intensive evanescent field of the optical sensor the adjustment of the transparent polymer waveguide thickness and the difference of the refractive index $\Delta n$ of said transparent polymer waveguide and said transparent polymer substrate is important.

The thickness of the transparent polymer waveguide may be selected so that X is in the range of 1 to 9, preferably in the range of 1.2 to 6, more preferably 1.5 to 4.5 and most preferably 2 to 3.5, whereby d is calculated based on the equation:

$$X = \frac{d\, n_2^{2\pi}}{\lambda}$$

in which d is the thickness of the transparent polymer waveguide in nm, $n_2$ is the refractive index of the transparent polymer waveguide and $\lambda$ is the wavelength in nm, wherein the wavelength is in the range of 360 nm to 1000 nm, preferably 400 nm to 800 nm and more preferably 600 nm to 750 nm.

The thickness of the thin transparent polymer waveguide can be of $\geq 0.12\,\mu m$ and $\leq 0.40\,\mu m$, preferably $\geq 0.14\,\mu m$ and ≦0.30 µm, more preferably ≧0.16 µm and ≦0.28 µm and most preferably ≧0.18 µm and ≦0.24 µm for a wavelength of 633 nm.

However, it can be beneficial that the smaller the difference of the refractive index Δn of said transparent polymer waveguide and said transparent polymer substrate the larger can be the thickness of the polymeric waveguide.

It may be preferred that the thickness of the thin transparent polymer waveguide can be of ≧0.13 µm and ≦0.29 µm. An increased intensive evanescent field of the optical sensor can be obtained for the thin transparent polymer waveguide with a thickness of ≧0.17 µm and ≦0.22 µm.

The thickness of the transparent polymer substrate can be of ≧2 µm and ≦5 mm. However, it can be preferred that the thickness of the transparent polymer substrate is of ≧20 µm and ≦3 mm and more preferred of ≧50 µm and ≦1.5 mm. The thickness of the transparent polymer substrate can also be of ≧100 µm and ≦500 µm.

It can be preferred that the lower surface of said transparent polymer waveguide completely contacts the upper surface of the transparent polymer substrate.

The other critical feature is the refractive index difference of Δ n 0.1 to Δ n 0.5, preferably of Δ n 0.2 to Δ n 0.4 and more preferably of Δ n 0.25 to Δ n 0.35 with respect to said transparent polymer waveguide and the transparent polymer substrate in order to obtain a sufficient high evanescent intensity for qualitative and/or quantitative determination of chemical or biochemical compounds with the optical sensor according to the present invention.

Further, it is important that the refractive index n of the transparent polymer waveguide is higher than the refractive index n of the transparent polymer substrate, which contacts the lower surface of said waveguide.

The superstrate surrounding the optical sensor is generally water having a refractive index of n 1.33.

The refractive index is measured if not other way stated at a temperature of 23° C. and at a wavelength of 632.8 nm.

It is one advantage of the optical sensor according to the present invention that the above mentioned selection of defined material characteristics provide an optical biosensor which has a high performance for detecting specific chemical and/or biochemical substance whit high qualitative and/or quantitative precision.

A further advantage is, that the optical sensor according to the present invention has a low vertical range of manufacture, since the polymeric waveguide can be applied by spin coating or printing to the molded or cast polymeric substrate. However, it is also possible to cast or mold the polymeric substrate on the spin coated or printed polymeric waveguide.

The preferred method of providing an optical sensor according to the present invention comprises:
  the polymeric optical waveguide is spin-coated or printed on the upper surface of the transparent polymer substrate; and/or
  the polymeric substrate is molded or cast on a polymeric waveguide layer; and/or
  the grating structure is replicated from a micro structured mold.

A further embodiment of the optical sensor can be used for the surface plasmon resonance based detection of the presence of chemical- and/or bio-molecules at the surface of the waveguide. In this case the surface is covered with a thin metal layer, preferably Au.

One benefit of the optical sensor according to the present invention is that the polymer materials match the chemical and thermo-mechanical properties. Thus, failure during the various treatments which are required for the application of biosensing on top of the waveguide is significantly reduced compared to optical sensors having an inorganic waveguide layer. The latter problems of inorganic waveguide layers are due to an inherent difference in thermal expansion of the inorganic waveguide layer and substrate, which leads to stresses in the layer and a high mechanical stress in the interface, which leads to cracking and delamination. Therefore, transparent polymeric waveguiding layers are much more robust in the chemical environment which is determined by the biochemistry involved for the analysis. The thermo-mechanical properties of polymeric layers in particular the high strain to failure make the optical sensor device very stable under temperature cycling conditions as compared to inorganic layers. Thus, they show good mechanical strength so that temperature variations do not lead to crazing or other mechanical failure. The waveguide layer shows a good adhesion to the substrate as due to their low modulus of elasticity only low stress levels develop in the interface and due to their hydrophobic character the optical sensor is not sensitive to water attack in the interface of the transparent polymer waveguide layer and the attached transparent polymer substrate.

Another benefit of the all-plastic optical sensor according to the present invention the polymer materials are not expensive and easy to manufacture, compared to inorganic waveguide materials. This makes the optical sensor according to the present invention attractive for application in the medical field as disposable as required for diagnostic applications.

A further benefit of using a polymer waveguide layer is that it can be applied by spin-coating technology, which is much easier in the manufacture, thus more cost effective than high-vacuum assisted application technology, which is required for inorganic layers.

Such organic waveguide layer can be applied on a transparent polymer with a low refractive-index substrate to give sufficient evanescent intensity for application for example in a biosensing device based on immobilized bioreceptors at the surface of the waveguiding layer.

The optical sensor and the substrate according to the present invention can preferably have a planar form.

Within the scope of this invention, the optical sensor can be in form of a strip, a plate, a round disc or of any other geometrical form. The chosen geometrical form is intrinsically not crucial and can be governed by the intended sensor use. It may, however, also be used as an independent element, spatially separated from the source of excitation light and from the optoelectronic detection system.

The thin transparent polymer waveguide can have at least one recess and/or at least one heightening on the outer upper surface of said waveguide.

Further the thin transparent polymer waveguide can have at least one recess and/or at least one heightening on the lower upper surface of said waveguide contacting the transparent polymer substrate, wherein the heightening/s engage with a positive fit into the transparent polymer substrate contacting said polymer waveguide and the transparent polymer substrate engage with a positive fit into the lower upper surface of said waveguide. The recess can be important for enhancing the coupling of the light wave into said transparent polymer waveguide, wherein the depth of said recess is less than the thickness of the said transparent polymer waveguide. It is preferred that a grating structure of a plurality of recesses for enhancing the coupling of the light wave into said transparent polymer waveguide is formed on the upper and/or lower surface of the polymeric wave guide.

According to a preferred embodiment of the present invention the top surface of the heightening/s does not exceed the upper outer surface of the polymeric waveguide.

It can be preferred that a surface area of said transparent polymer waveguide of at least 5% to 95%, preferably 5% to 25%, more preferably 5% to 15% of the upper outer surface and/or lower inner surface of said transparent polymer waveguide comprises a grating structure of a plurality of recesses for enhancing the coupling of the light wave into said transparent polymer waveguide.

The grating period can be from 250 nm to 950 nm, more preferred from 300 nm to 750 nm and most preferred from 350 nm to 450 nm. The grating exhibits one periodicity only, i.e. is monodiffractive. However it can be preferred that the grating exhibits more than one periodicity, such as tow or three periodicities and/or a gradual variation of the periodicity.

The specific binding compounds to detect at least one specific chemical and/or biochemical substance can be bonded direct to the outer upper surface of the polymeric waveguide or contacted to the outer upper surface of the polymeric waveguide, for example by means of adsorption, and/or can be stuck to the outer upper surface of the polymeric waveguide, for example by direct chemical reaction or via a chemical linker molecules. This can be done in a patterned fashion and for a multitude of different kinds of specific probes by printing techniques.

In order to have a minimum vertical range of manufacture it is most preferred that the optical sensor according to the present invention does not comprise a waveguide with a cladding layer thereon having at least one area of depletion in form of nanowells, wherein bound molecules are placed within said depletion area as detecting material. Thus, the optical sensor according to the present invention exclude a waveguide capable of guiding and channeling light and having on the surface of said waveguide a cladding layer having at least one area of depletion wherein a substance placed within said depletion area can be illuminated by the evanescent wave of light channeled in said waveguide.

Further, it may be preferred that the grating or recess is free of detecting material.

In another preferred embodiment the detecting material may be applied on the grating structure.

Typically, the attenuation of the guided light wave in the waveguide is less than 0.5 dB/cm, preferably less than 0.01 dB/cm measured with a light source emitting at 633 nm, thereby resulting in a long distance of the guided beam and a low scattering of the guided wave into the media surrounding it. In particular, it is preferred under these conditions to guide the TE and/or TM mode.

The thickness of the waveguide according to the present invention is small enough so that only one TM mode and/or one TE mode can propagate in the waveguide.

A suitable substrate is typically any kind of polymeric material. It is preferred to use a polymer that has as low an optical refractive index as possible and/or as low an intrinsic luminescence as possible, and which can be optically treated in as simple a manner as possible, for example extruding or for injection molding. The substrate must be transparent at least at the excitation and emission wavelength.

In the sense of the present invention the term "transparent polymer" includes thermoplastic, thermosetting and/or structurally cross-linked plastic.

The transparent polymer material for the substrate is preferably selected from the group comprising olefines, cyclic olefines, acrylates, methacrylates, ethers, esters, urethanes, ether-esters, ether-urethanes, urethane acrylates, enols, etc. and partially or perfluorinated analogons of these materials, silicones, silicone-acrylates and -methacrylates.

More preferred as transparent polymer material are halogenated polymers, in particular fluorinated or perfluorinated polymers. Thus, most preferred are halogenated acrylates, halogenated methacrylates, acrylates with perfluorinated side chains and/or methacrylates with perfluorinated side chains as well as copolymers thereof, for example with low refractive index $n_D$=1.37–1.41.

The transparent material of the substrate has a lower refractive index than the transparent polymeric waveguide, i.e. a refractive index $n_D$ of at most 1.69.

Most preferred, the transparent polymer material of the substrate is cross-linked.

A suitable transparent waveguide material is typically any kind of polymeric material with a higher refractive index than the transparent polymeric substrate. It is preferred to use a polymer that has as high an optical refractive index as possible. Also, it is preferred that it can be optically processed in as simple manner as possible, for example spin coating on top of the upper outer surface of the transparent polymeric substrate. The substrate must be highly transparent at least at the excitation wavelength and shows preferably no autofluorescence. More preferably it is also transparent for the emission wavelength.

In the sense of the present invention the term "transparent waveguide" includes thermoplastic, thermosetting and/or structurally cross-linked plastic having all a higher refractive index than the transparent polymeric substrate, i.e. a refractive index $n_D$ of at least 1.39.

The transparent polymer material for the waveguide is preferably selected from the group comprising homocyclic and/or heterocyclic aromatics, halogenated and/or sulphur containing polymers. Bromium and/or sulphur containing polymers, in particular bromium and/or sulfur containing polymers with limited delocalised pi-system are preferred.

More preferred materials for the waveguide are Poly (penta-bromophenyl methacrylate ($n_D$=1.71), Poly(vinylphenylsulfide) ($n_D$=1.657), Bisphenol-S based epoxides and/or -acrylates or such like.

The outer upper surface of said transparent polymer waveguide possesses specific binding compounds to detect at least one specific chemical and/or biochemical substance.

The surface of said transparent polymer waveguide can be treated and covered with specific, for example adhesion, layers to bind for instance biomolecules, like antibodies or cDNA strands for selective binding or hybridization of biological targets in sample liquids which are directed over the treated surface of the device for the analysis of the liquid of interest. The presence of bound biomolecules is detected for instance by the fluorescence excited by the evanescent field of the waveguide of the sensor according to the present invention.

Within the scope of this invention the term "sample" shall be taken to mean the entire solution to be assayed, which may contain a substance to be, detected—the analyte. The detection can be made in a single-step or multistep assay in the course of which the surface of the optical sensor according to the present invention is contacted with one or more solutions. At least one of the solutions employed can contain a substance having luminescence properties, which can be detected in the practice of this invention.

If a substance having luminescence properties is already adsorbed on the upper waveguide surface, then the sample may also be free from luminescent components. The sample can contain further constituents, typically pH buffers, salts, acids, bases, surface-active substances, viscosity-influencing modifiers or dyes. In particular, a physiological saline solution can be used as solvent. If the luminescent constituent itself is liquid, then the addition of a solvent can be dispensed with.

The sample may further contain a biological medium, for example egg yolk, a body fluid or constituents thereof, in particular blood, serum, plasma or urine. Furthermore, the sample may consist of surface water, solutions of extracts of natural or synthetic media such as soil or parts of plants, bioprocess broths or synthesis broths.

The sample can either be undiluted or used additionally with a solvent.

Suitable solvents are water, aqueous buffer and protein solutions and organic solvents.

Suitable organic solvents are alcohols, ketones, esters, and aliphatic hydrocarbons. It is preferred to use water, aqueous buffers or a mixture of water and a water-miscible organic solvent. The sample can, however, also contain constituents that are insoluble in the solvent, for example pigment particles, dispersants, natural and synthetic oligomers or polymers. In this case the sample is in the form of an optically turbid dispersion or emulsion.

Suitable luminescent compounds are luminescent dyes having a luminescence in the wavelength range from 360 nm to 1000 nm, typically including rhodamines, fluorescein derivatives, coumarin derivatives, distyryl biphenyls, stilbene derivatives, phthalocyanines, naphthalocyanines, polypyridyl-ruthenium complexes such as tris(2,2'-bipyridyl)ruthenium chloride, tris(1,10-phenanthroline) ruthenium chloride, tris(4,7-diphenyl-1,10phenanthroline) ruthenium chloride and polypyridyl-phenazine-ruthenium complexes, platinum-porphyrin complexes such as octaethyl-platinum-porphyrin, long-life europium and/or terbium complexes or cyanine dyes. Suitable for analyses in blood or serum are dyes having absorption and emission wavelengths in the range from 360 nm to 1000 nm.

Particularly suitable luminescent compounds are dyes such as fluorescein derivatives, which contain functional groups with which they can be covalently bonded, for example fluorescein isothiocyanate.

The preferred luminescence is fluorescence.

The luminescent dyes eligible for use may also be chemically bonded to polymers or to one of the binding partners in biochemical affinity systems, e.g. antibodies or antibody fragments, antigens, proteins, peptides, receptors or their ligands, hormones or hormone receptors, oligonucleotides, DNA strands and RNA strands, DNA or RNA analogs, binding proteins such as protein A and G, avidin or biotin, enzymes, enzyme cofactors or 0 inhibitors, lectins or carbohydrates. The covalent luminescent labelling last mentioned is the preferred utility for reversible or irreversible (bio) chemical affinity assays. It is further possible to use luminescent-labelled steroids, lipids and chelators. Intercalating luminescent dyes are also of particular interest for hybridisation assays with DNA strands or oligonucleotides, especially if—like different ruthenium complexes—they exhibit enhanced luminescence in the intercalation. If these luminescent-labelled compounds are brought into contact with their affinity partners immobilised on the surface of the optical sensor according to the present invention, then the binding can be determined quantitatively from the measured intensity of luminescence. A quantitative determination of the analyte is also possible by measuring the change in luminescence when the sample interacts with the luminophores, for example in the form of luminescence quenching with oxygen or of luminescence enhancement by conformation modifications of proteins.

It is preferred to use coherent light for the luminescence excitation, more particularly laser light of wavelength 300 to 1100 nm, more particularly still of 400 to 850 nm and, most preferably, of 550 to 700 nm.

Lasers, which may suitably be used, are dye lasers, gas lasers, solid lasers and semiconductor lasers. Where necessary, the emission wavelength can also be doubled by nonlinear crystal optics. The beam can also be still further focused by optical elements, polarised, or attenuated by grey filters. Particularly suitable lasers are argon-ion lasers and helium-neon lasers which emit at wavelengths between 457 nm and 514 nm and, respectively, between 543 nm and 633 nm. Very particularly suitable lasers are diode lasers or frequency-doubled diode lasers of semiconductor material that emit at a fundamental wavelength between 630 nm and 1100 nm, as they permit a substantial miniaturisation of the entire sensor system on account of their small dimensions and low power consumption. However diode lasers with about 405 nm and sufficient power can be used also.

In the process of this invention the sample can be brought into contact with the optical sensor in the immobile state as well as guided continuously over it, and the cycle can be open or closed.

A specific embodiment of the process consists in immobilising the substances having luminescent properties used for detecting the analyte direct at the surface of the waveguiding layer. The substance having luminescent properties can be, for example, a luminophore which is bound to a protein and which can thereby be excited to luminescence in this manner at the surface of the waveguiding layer. If a partner having affinity for the protein is guided over this immobilised layer, then the luminescence can be modified and the amount of said partner could be determined in this manner. In particular, both partners of an affinity complex can also be labelled with luminophores so as to be able to effect the determination of concentrations from the energy transfer between the two, e.g. in the form of luminescence quenching.

Another preferred embodiment of the process for carrying out chemical or biochemical affinity assays consists in immobilising on the surface of the optical sensor, i.e. upper outer surface of the waveguide, a specific binding partner as chemical or biochemical detector substance for the analyte itself or for one of the binding partners. The assay can be a single-step or multistep assay in the course of which, in successive steps, one or more than one solution containing binding partners for the detector substances immobilised on the surface of the optical sensor according to the present invention is guided, the analyte becoming bound in one of the partial steps. Binding luminescent-labelled participants in the affinity assay effects the detection of the analyte. The luminescent-labelled substances used may consist of one or more than one binding partner of the affinity assay, or also of an analogue of the analyte provided with a luminophore. The sole criterion is that the presence of the analyte leads selectively to a luminescence signal or selectively to a change in the luminescence signal.

The immobilisation of the detector substances may typically be carried out by hydrophobic absorption or covalent bonding direct on the upper outer waveguide surface or after chemical modification of the surface, for example by silanisation or applying a polymer layer. In addition, a thin interlayer consisting e.g. of $SiO_2$ can be applied as adhesion-promoting layer direct to the upper outer waveguide surface to facilitate the immobilisation of the detector substances direct on the waveguide.

Suitable detector substances are typically antibodies for antigens, binding proteins such as protein A and G for immunoglobulins, receptors for ligands, oligonucleotides and single strands of RNA and DNA for their complementary strands, avidin for biotin, enzymes for enzyme substrates, enzyme cofactors or inhibitors, lectins for carbohydrates. Which of the respective affinity partners is immobilised on the surface of the optical sensor according to the present invention will depend on the architecture of the assay.

The assay itself can be a single-step complexing process, for example a competitive assay, or also a multistep process, for example a sandwich assay.

In the simplest case of the competitive assay, the sample which contains the analyte in unknown concentration as well as a known amount of a compound that is similar except for luminescent labelling is brought in to contact with the surface of the optical sensor according to the present invention, where the luminescent labelled and unlabelled molecules compete for the binding sites at their immobilised detector substances. A maximum luminescence signal is achieved in this assay configuration when the sample contains no analyte. With increasing concentration of the substance to be detected, the luminescence signals under observation become lower.

In a competitive immunoassay it does not necessarily have to be the antibody, which is immobilised: the antigen too can be immobilised on the surface of the optical sensor according to the present invention as detector substance. Usually it is immaterial which of the partners is immobilised in chemical or biochemical affinity assays. This is a basic advantage of luminescence-based assays over methods such as surface plasmon resonance or interferometry, which are based on the change in adsorbed mass in the evanescent field of the waveguiding layer.

Further, in the case of competitive assays the competition does not need to be limited to binding sites at the surface of the optical sensor according to the present invention. For example, a known amount of an antigen can also be immobilised on the surface of said sensor and then brought into contact with the sample which contains an unknown amount to be detected of the same antigen as analyte as well as luminescent-labelled antibodies. In this case the competition between antigens that are immobilised on the surface and present in solution takes place for binding of the antibodies.

The simplest case of a multistep assay is a sandwich immunoassay in which a primary antibody is immobilised on the surface of the optical sensor according to the present invention. The binding of the antigen to be detected and of the luminescent-labelled secondary antibody used for carrying out the detection to a second epitope of the antigen can be effected either by successive contacting with the solution containing the antigen and a second solution containing the luminescent-labelled antibody, or by combining these two solutions beforehand, so that, finally, the partial complex consisting of antigen and luminescent-labelled antibody is bound. Affinity assays may also comprise further additional binding steps. For example, in the y W case of sandwich immunoassays protein A, which specifically binds immunoglobulins which then act as primary antibodies in a subsequent sandwich assay, which is carried out as described above, at their so called $F_c$ part, can be immobilised on the surface of the optical sensor according to the present invention in a first step.

There is a whole host of further types of affinity assays, typically using the known avidin-biotin affinity system.

It is furthermore possible to use the surface of the optical sensor according to the present invention not only for single use but also to regenerate it. Under suitable conditions, for example low pH, elevated temperature, using organic solvents or so-called chaotropic reagents (salts), it is possible to dissociate the affinity complexes selectively without substantial impairment of the binding capacity of the immobilised detector substances. The exact conditions are strongly dependent on the particular affinity system.

Another essential embodiment of the process consists on the one hand in limiting the production of the signal—in the case of back-coupling this also applies to signal detection—to the evanescent field of the waveguide and, on the other, in the reversibility of the affinity complex formation as equilibrium process. Using suitable rates of flow in a continuous flow system it is possible to monitor in real time the binding or desorption or dissociation of bound luminescent-labelled affinity partners in the evanescent field. The process is therefore suitable for kinetic studies for determining different association or dissociation constants or also for displacement assays.

In a preferred embodiment a cover plate is applied containing channels for guidance of the analyte and other liquids necessary for carrying out the measurement in a closed microfluidic system.

The detector including optical elements for detecting the luminescent signal coming from the surface of the waveguide can be placed above the waveguiding layer or below the substrate.

The most important design criteria are the intensity of the evanescent field at the surface of the waveguide. This intensity is determined by the refractive indices of the waveguide layer (n2), the substrate (n1) and the superstrate (n3), the thickness of the waveguide layer (d).

The refractive index is measured if not other way stated at a temperature of 23° C. and at a wavelength of 632.8 nm. Further, the thickness of the waveguide layer is in μm if not other way stated.

This intensity decays exponentially with increasing distance from the surface. For design optimization one can take the average intensity of the evanescent field in a range of the expected thickness of adsorbed biomolecules in which the dye molecules are to be excited by the same field.

A preferred embodiment of an optical sensor according to the present invention is outlined below:

Substrate:
glass treated with silan adhesion promoter;
low index substrate: 2,2,3,3,4,4,5,5-octafluoro-1,6-hexanedioldimethacrylate (ABCR)
High index waveguide:
poly-pentabromophenylacrylate (Aldrich);
Irgacure 184 (Ciba) was added to the monomer to enable photopolymerization.

The high index polymer was dissolved in cyclohexanone at a concentration of 20% (w/w). The refractive indices of the final cross-linked polymer and the high index polymer are 1.44 and 1.70 respectively. The final thickness of the cross-linked polymer substrate is about 2 μm and that of the high index polymer is about 210 nm. The replication master was obtained by E-beam lithography on a silicon wafer.

Figure 1:
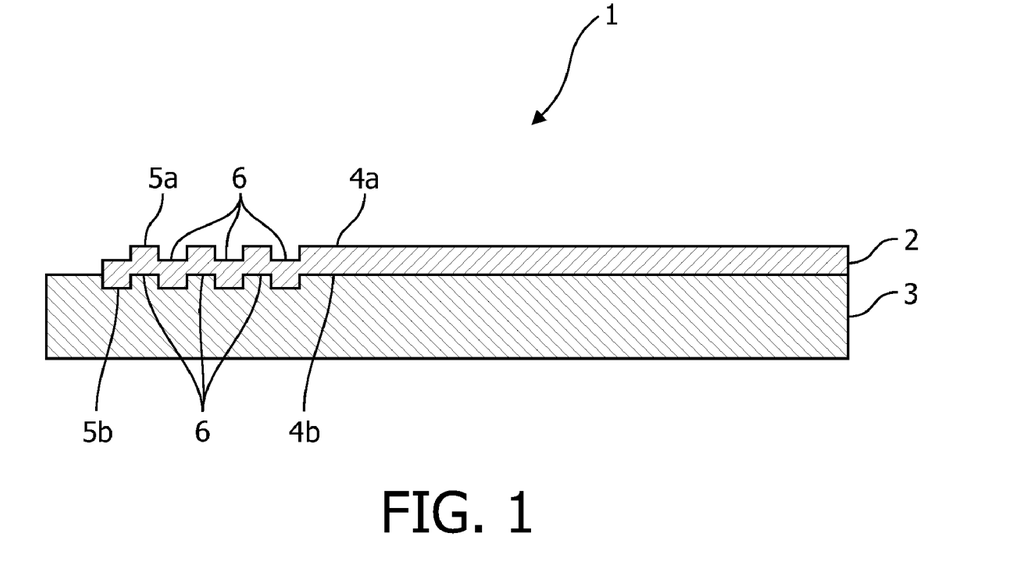
FIG. 1 shows a first optical sensor according to the present invention.

FIG. 1 shows a two layer optical sensor 1 of a polymer waveguide 2 of polyethersulfone (PES) with a thickness of 0.25 µm and a refractive index of $n_2=1.65$ on a polymer substrate 3 of polymethylmethacrylate (PMMA) with a thickness of 1 mm and a refractive index of $n_3=1.49$. The upper outer surface 4a of the polymer waveguide 2 and the lower inner surface 4b of the polymer waveguide 2 comprises at one end a grating structure of elevations 5a and depressions 5b of a plurality of recesses 6 for enhancing the coupling of the light wave into said transparent polymer waveguide. On top of the upper outer surface 4a of the polymer waveguide 2 binding compounds to detect a specific chemical substance are coated (not shown). In use (not shown) at least the upper surface of the polymer waveguide 2 of the optical sensor 1 with binding compounds thereon is contacted with a superstrate, such as water ($n_1=1.33$).

Figure 2:
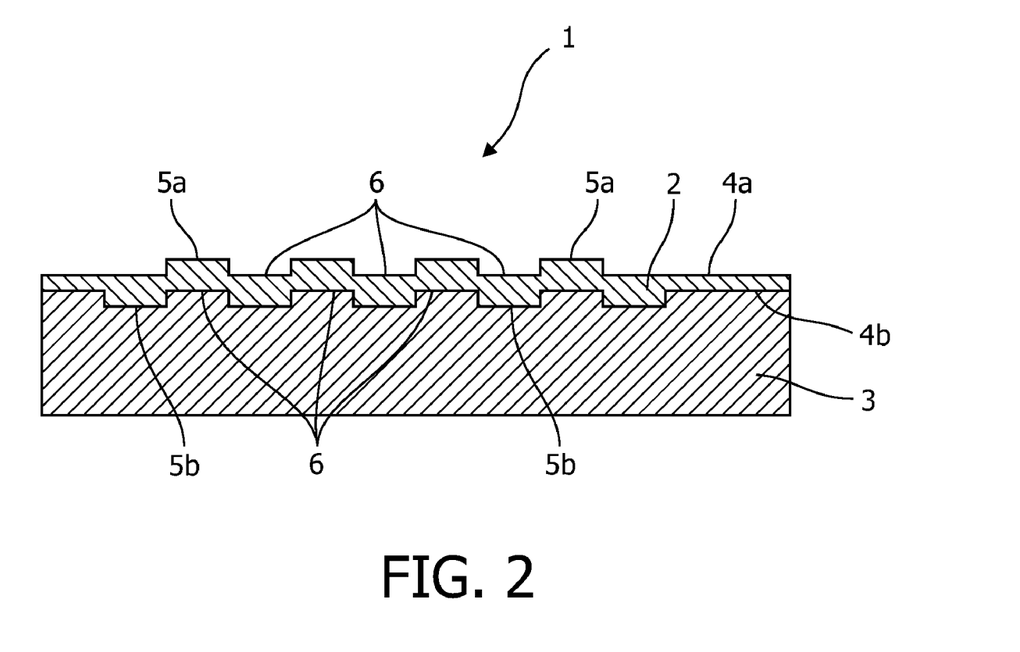
FIG. 2 shows a second optical sensor according to the present invention.

FIG. 2 shows a two layer optical sensor 2, which differs from FIG. 1 in that the elevations 5a of the grating structure protrude the upper outer surface 4a of the polymer waveguide 2.

Figure 3:
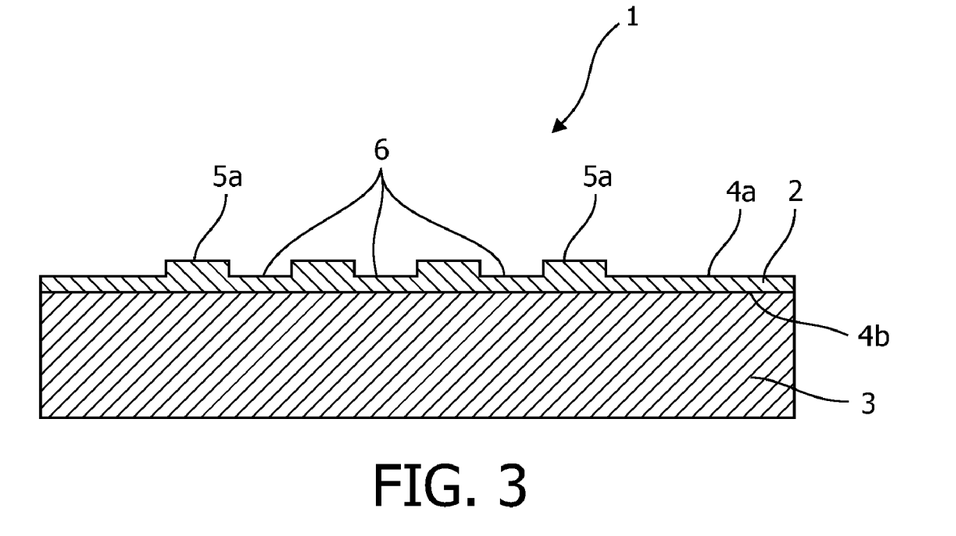
FIG. 3 shows a third optical sensor according to the present invention.

FIG. 3 shows a two layer optical sensor 2, which differs from FIG. 1 in that the elevations 5a of the grating structure protrude the upper outer surface 4a of the polymer waveguide 2 and no depressions 5b, i.e. the lower inner surface 4b of the polymer waveguide 2 comprises no grating structure.

Figure 4:
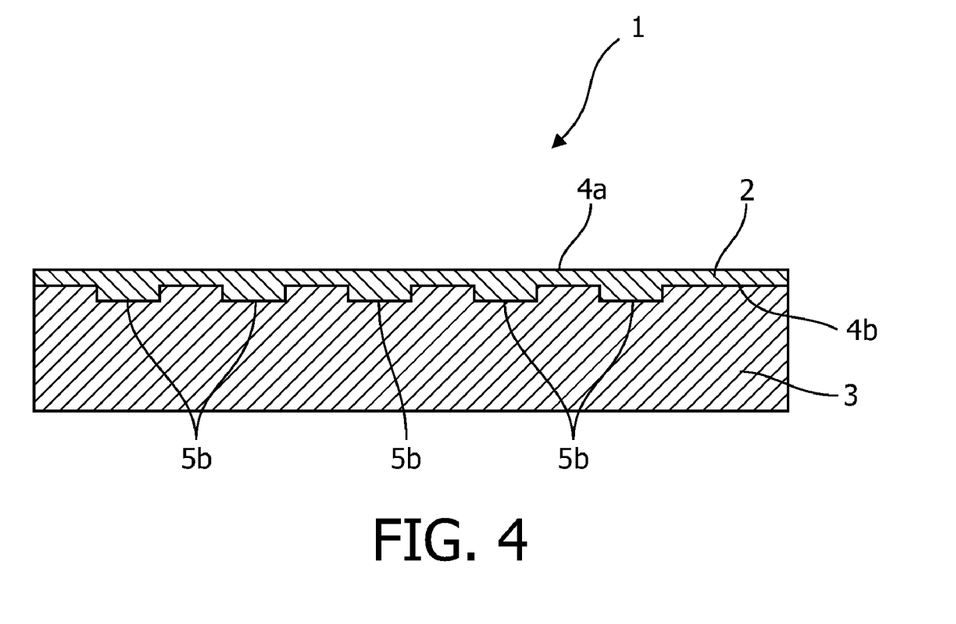
FIG. 4 shows a fourth optical sensor according to the present invention.

FIG. 4 shows a two layer optical sensor 2, which differs from FIG. 1 in upper outer surface 4a of the polymer waveguide 2 has no grating structure, i.e. no depressions 5b, but the lower inner surface 4b of the polymer waveguide 2 has a grating structure with depressions 5b as shown in FIG. 1.

Figure 5:
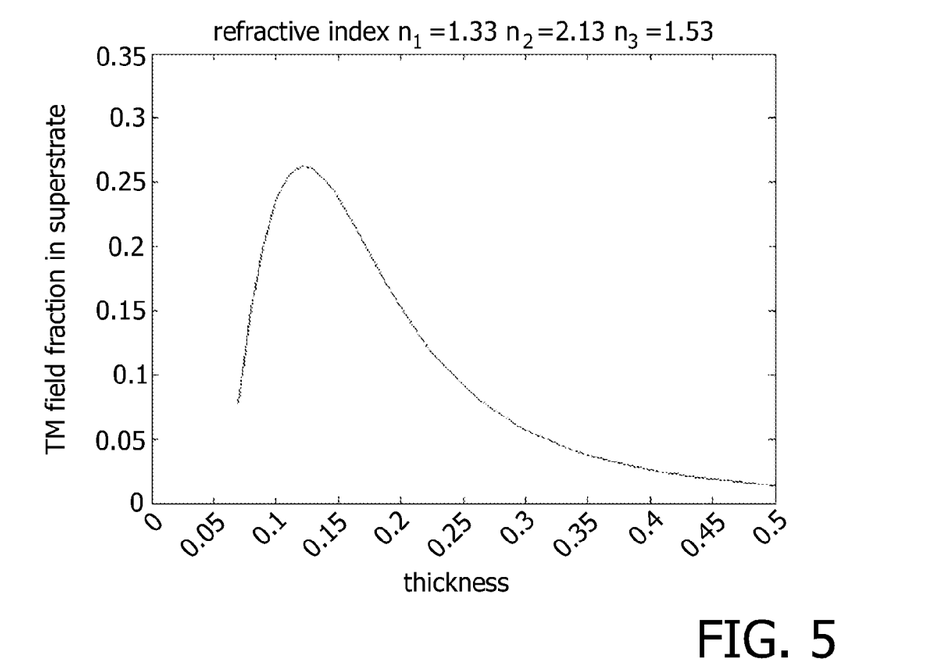
FIG. 5 shows the Evanescent intensity for a prior art optical sensor with an inorganic waveguide and a Zeonex 280 substrate.

FIG. 5 shows the function of a calculation for the transverse magnetic field polarized (TM) total evanescent field fraction in relation to the thickness of the waveguide of a prior art optical sensor. The optical sensor comprises an inorganic waveguide of $Ta_2O_5$ applied on a substrate of Zeonex 280 with a thickness of 0.5 mm much larger than the wavelength of the light, wherein the substrate has a refractive index $n_3$ of 1.53 and the inorganic waveguide $Ta_2O_5$ has a refractive index $n_2$ of 2.13 surrounded by water having a refractive index of $n_1=1.33$.

Figure 6:
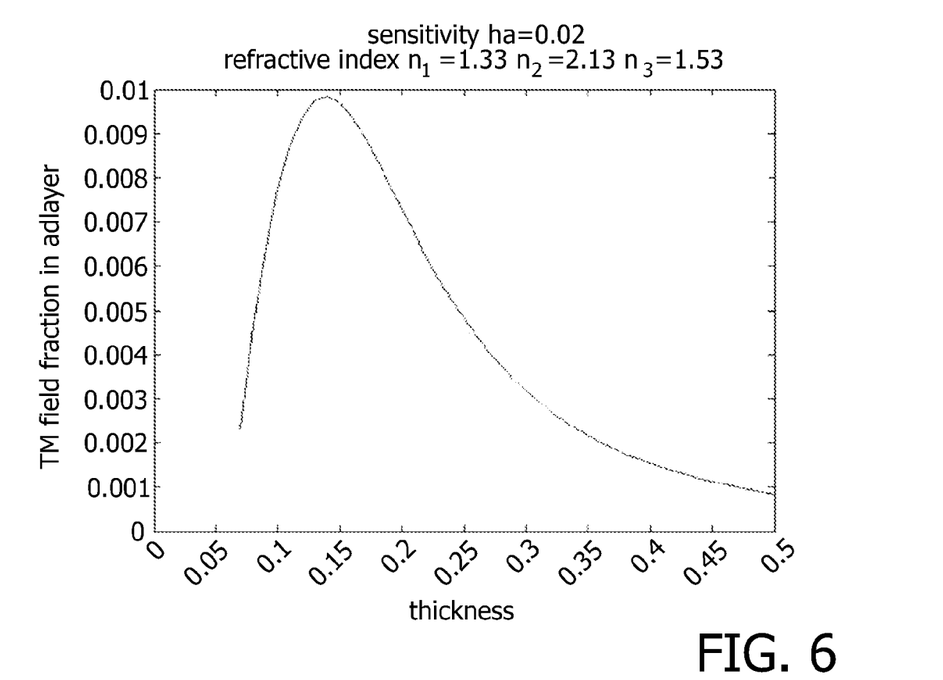
FIG. 6 shows the Evanescent intensity in 20 nm of the superstrate water for the prior art optical sensor of FIG. 5.

FIG. 6 shows the function of a calculation for the evanescent TM field fraction in first 20 nm perpendicular to the upper outer surface of the waveguide depending on the thickness of the waveguide of FIG. 5.

Figure 7:
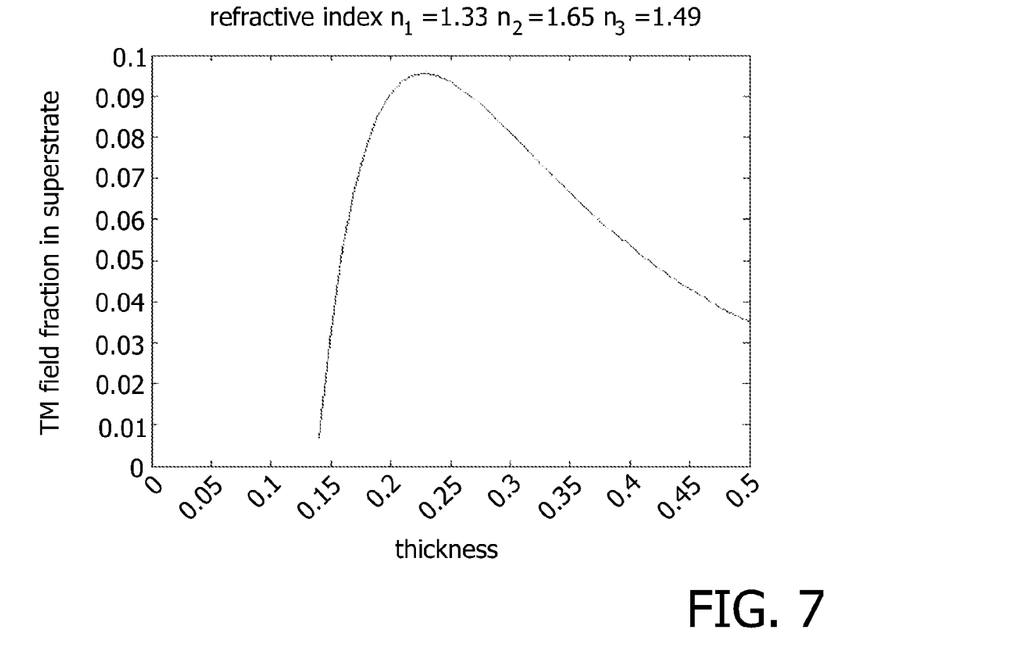
FIG. 7 shows the Evanescent intensity for a first optical sensor according to the present invention.

FIG. 7 shows the function of a calculation for the total evanescent TM field fraction depending on the thickness of a waveguide of an optical sensor according to the present invention. The optical sensor comprises a polymeric waveguide applied on a polymeric substrate with a thickness of 0.5 mm much larger than the wavelength of the light, wherein the polymeric substrate has a refractive index $n_3$ of 1.49 and the polymeric waveguide has a refractive index $n_2$ of 1.65 surrounded by water having a refractive index of $n_1=1.33$.

It can be taken from FIG. 7 that the optimum thickness of the polymeric waveguide is about 0.25 µm.

Figure 8:
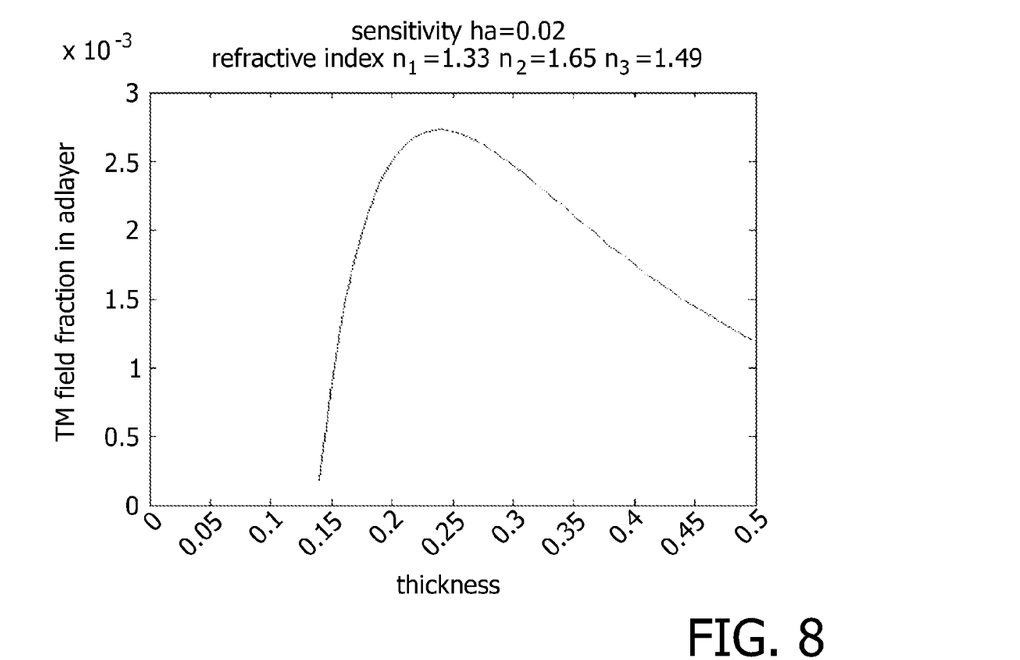
FIG. 8 shows the Evanescent intensity in 20 nm of the superstrate water for the optical sensor of FIG. 7.

FIG. 8 shows the function of a calculation for the evanescent TM field fraction in first 20 nm perpendicular to the upper outer surface of the waveguide depending on the thickness of the waveguide of FIG. 7.

Figure 9:
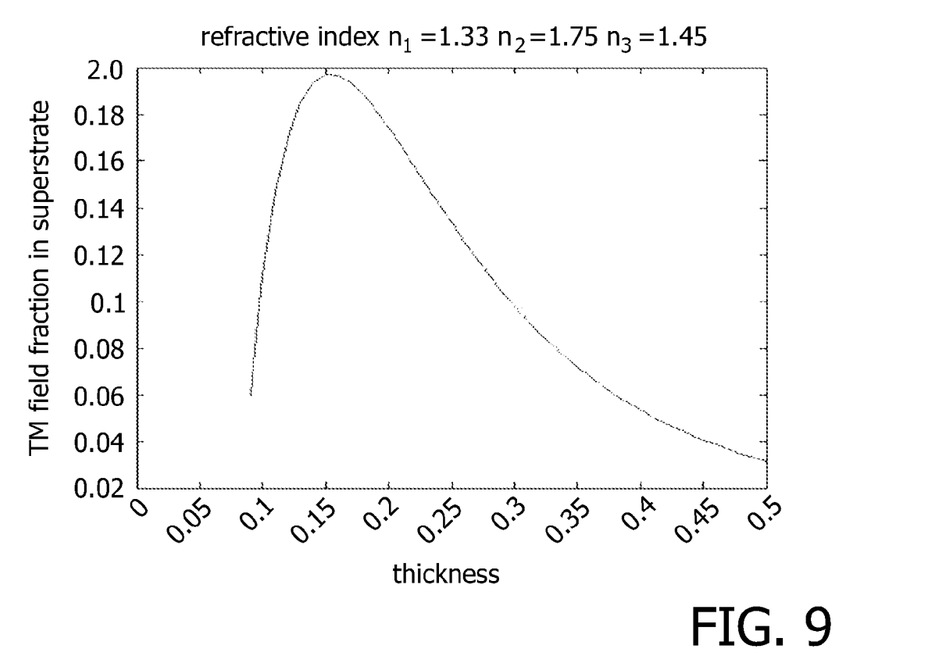
FIG. 9 shows the Evanescent intensity for a second optical sensor according to the present invention.

FIG. 9 shows the function of a calculation for the total evanescent TM field fraction depending on the thickness of a waveguide of an optical sensor according to the present invention. The optical sensor comprises a polymeric waveguide applied on a polymeric substrate with a thickness of 0.5 mm much larger than the wavelength of the light, wherein the polymeric substrate has a refractive index $n_3$ of 1.45 and the polymeric waveguide has a refractive index $n_2$ of 1.75 surrounded by water having a refractive index of $n_1=1.33$.

It can be taken from FIG. 9 that the optimum thickness of the polymeric waveguide is about 0.17 µm. Further, it can be taken from FIG. 9 that the evanescent field at the optimum thickness of the waveguide is twice as high compared to the optical sensor of FIG. 7.

Figure 10:
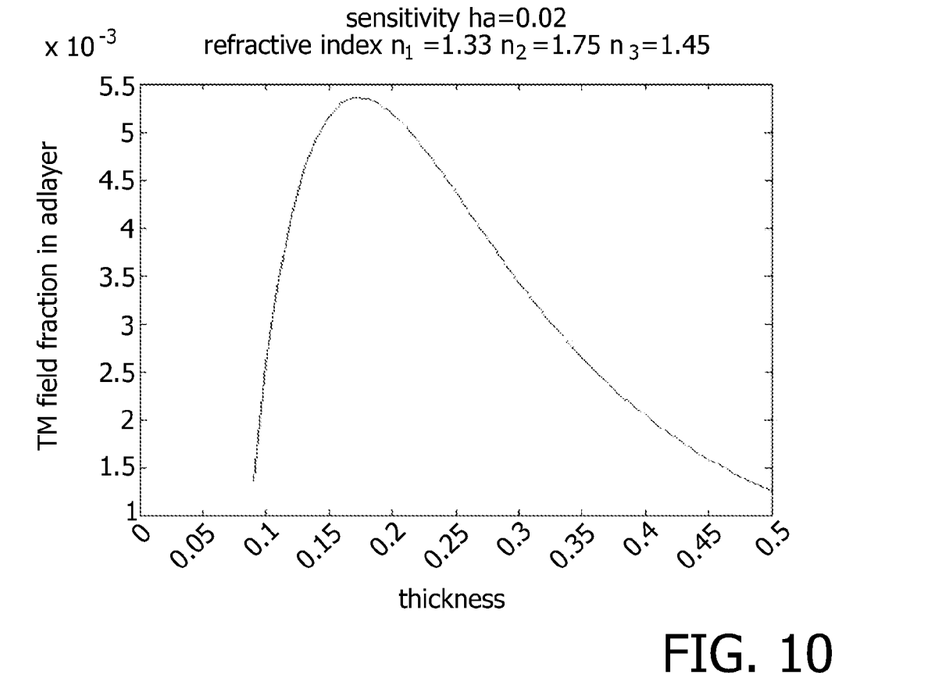
FIG. 10 shows the Evanescent intensity in 20 nm of the superstrate water for the optical sensor of FIG. 9.

FIG. 10 shows the function of a calculation for the evanescent TM field fraction in the first 20 nm perpendicular to the upper outer surface of the waveguide depending on the thickness of the waveguide of FIG. 9. The evanescent field in 20 nm at the optimum thickness of the waveguide is twice as high as compared to the optical sensor of FIG. 8.

According to the present invention it may be preferred that the evanescent intensity, i.e. TM field fraction in the superstrate water, over a distance of 20 nm perpendicular to the outer upper surface of said optical sensor therefrom should be adjusted to be in the range of 0.002 to 0.01, preferably in the range of 0.003 to 0.008, more preferred in the range of 0.004 to 0.007.

The TM field can be calculated according to W. Lukosz and K. Tiefenthaler "sensitivity of grating couplers as integrated-optical chemical sensors", J. Opt. Soc. Am. B6(2) (1989) pp. 209-220 in comparison to the benchmark of the optical sensor (see FIG. 2) consisting of a waveguide of $Ta_2O_5$ with a refractive index of $n_D$ 2.13 and a Zeonex 280 substrate[*1] with a refractive index of $n_D$ 1.53, whereby the superstrate is water with a refractive index of $n_D$ 1.33. [*1]: Zeonex 280 can be obtained from Nippon Zeon Co., LTD.

The fraction of the electric field in the superstrate of the waveguide may be preferably calculated using the equation:

$$I_{TM}^{sup} = \frac{(\varepsilon_2 - n_{eff}^2)\varepsilon_2}{(\varepsilon_2 - \varepsilon_1)n_{eff}^2} \frac{1}{q_1(n_{eff})[d.k_0 + \delta z_1(n_{eff}) + \delta z_3(n_{eff})]}$$

where $\delta z_1$ is the penetration depth in the superstrate and $\delta z_3$ is the penetration depth in the substrate, given by:

$$\delta z_1(n_{eff}) = \frac{1}{q_1(n_{eff})[n_{eff}^2(1/\varepsilon_1 + 1/\varepsilon_2) - 1]}$$

$$\delta z_3(n_{eff}) = \frac{1}{q_3(n_{eff})[n_{eff}^2(1/\varepsilon_3 + 1/\varepsilon_2) - 1]}$$

In these equation $q_1$ is the imaginary part of the wave vector in the superstrate and $q_3$ the imaginary part of the wave vector in the substrate given by:

$$q_1(n_{eff}) = \sqrt{n_{eff}^2 - \varepsilon_1}$$

$$q_3(n_{eff}) = \sqrt{n_{eff}^2 - \varepsilon_3}$$

The quantity $n_{eff}$ describes the effective refractive index of the propagating mode. The value for the propagation constant of the TM mode can be found by solving the following equation:

$$k_z(n_{eff})k_0 d - \phi_{m1}(n_{eff}) - \phi_{m3}(n_{eff}) - m\pi = 0$$

Here, m=0, 1, 2 . . . is the mode number and the phase functions $\phi_{m1}$ and $\phi_{m3}$ are given by:

$$\phi_{m1}(n_{eff}) = \tan^{-1}\left(\frac{\varepsilon_2 q_1(n_{eff})}{\varepsilon_1 k_z(n_{eff})}\right)$$

$$\phi_{m3}(n_{eff}) = \tan^{-1}\left(\frac{\varepsilon_2 q_3(n_{eff})}{\varepsilon_3 k_z(n_{eff})}\right) \text{ with}$$

$$k_z(n_{eff}) = \sqrt{\varepsilon_2 - n_{eff}^2}$$

In the equations the dielectric constants of the superstrate, wave guide layer and substrate are denoted by $\varepsilon_1$, $\varepsilon_2$ and $\varepsilon_3$ resp., $k_0$ is the wave vector in vacuum and d is the thickness of the wave guide layer.

In one of its aspects the invention relates to a process for detecting luminescence with an optical sensor according to the present invention by bringing a liquid sample into contact with the upper surface of the waveguide or upper surface of the bonding material attached to the upper surface of the waveguide, and measuring the luminescence produced by substances having luminescence properties in the sample, or by substances having luminescence properties immobilised on said waveguide, optoelectronically, wherein the excitation light is coupled into the said waveguide and traverses the waveguiding layer, whereby the substances having luminescence properties are excited to luminescence in the evanescent field of the waveguiding layer.

The detection of evanescently excited luminescence can be made by known methods and known detectors.

Detectors for the detection of the evanescently excited luminescence are for example Photodiodes, photocells, photomultipliers, CCD cameras and detector arrays, for example CCD cells, may suitably be used. The luminescence can be imaged with optical elements such as mirrors, prisms, lenses, Fresnel lenses and gradient index lenses thereon. To select the emission wavelength it is possible to use known elements such as filters, prisms, monochromatic filters, dichromatic mirrors and diffraction gratings.

In another of its aspects, the invention relates to the use of the optical sensor according to the present invention for the quantitative determination of chemical or biochemical compounds such as antibodies or antigens.

Yet another utility of the optical sensor according to the present invention is for the quantitative determination of receptors or ligands, oligonucleotides, strands of DNA or RNA, DNA or RNA analogs, enzymes, enzyme substrates, enzyme cofactors or inhibitors, lectins and carbohydrates.

In a further aspect, the invention relates to the use of the optical sensor according to the present invention for the selective quantitative determination of luminescent constituents in optically turbid fluids.

Optically turbid fluids may typically be biological fluids such as egg yolk, body fluids such as blood, serum or plasma, and also samples emanating from environmental analysis, including surface water, dissolved soil extracts and dissolved plant extracts. Suitable fluids are also the reaction solutions obtained in chemical production, in particular dye solutions or reaction solutions originating from the production of fluorescent whitening agents. Also suitable are all types of the dispersions and formulations typically used in the textile industry, provided these contain one or more than one luminescent component.

The optical sensor according to the present invention can also be used for quality safeguarding.

In summary the optical sensor according to the present invention can for example be used for:
chemical or biological analysis, comprising analysis of biological fluids such as egg yolk, blood, serum or plasma;
environmental analysis, comprising analysis of water, dissolved soil extracts and dissolved plant extracts;
reaction solutions, dispersions and/or formulations analysis, comprising analysis in chemical production, in particular dye solutions or reaction solutions; and/or
quality safeguarding analysis.

Another aspect of the present invention is directed to a system comprising at least one light source, one optical sensor of the present invention as described above and at least one detector for the detection of the evanescently excited luminescence as described in the description above.

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. An evanescent field induced optical sensor for use as biosensor for detecting biological molecules, the optical sensor comprising:
 a transparent polymer substrate; and
 a thin transparent polymer waveguide coating at least a portion of the transparent polymer substrate, wherein the transparent polymer waveguide has a refractive index n of 1.4 to 1.79 the transparent polymer waveguide has a coupling grating recess structure for the coupling of light wave into the transparent polymer waveguide, a lower surface of the transparent polymer waveguide contacts the transparent polymer substrate, the transparent polymer substrate has a refractive index n of 1.29 to 1.69 and an upper surface of the polymer waveguide or optical sensor possess specific binding compounds to detect at least one specific chemical, wherein the lower surface of the waveguide possess at least one recess for enhancing the coupling of the light wave into the transparent polymer waveguide, wherein a depth of the at least one recess is less than the thickness of the transparent polymer waveguide and wherein the transparent polymer substrate engages into the at least one recess.

2. The optical sensor according to claim 1, wherein the thickness of the transparent polymer waveguide is selected so that X is in the range of 1 to 9, whereby d is calculated based on the equation:

$$X = \frac{d_{n_2} 2\pi}{\lambda}$$

in which d is the thickness of the transparent polymer waveguide in nm, $n_2$ is the refractive index of the transparent polymer waveguide and $\lambda$ is the wavelength in nm.

3. The optical sensor according to claim 1, wherein the upper surface of the waveguide possess at least one recess for enhancing the coupling of the light wave into the transparent polymer waveguide, wherein the depth of the recess is less than the thickness of the transparent polymer waveguide.

4. The optical sensor according to claim 1, wherein the transparent polymer waveguide has a thickness of $\geq 0.10$ μm and $\leq 0.50$ μm.

5. The optical sensor according to claim 1, wherein the material of the transparent polymer waveguide and the transparent polymer substrate is selected such that the difference of the refractive index Δn of the transparent polymer waveguide and the transparent polymer substrate is at least Δn 0.1.

6. The optical sensor according to claim 1, wherein the polymer of the transparent polymer substrate is cross-linked.

7. The optical sensor according to claim 1, wherein at least one of
   the polymeric material of the transparent polymer substrate is selected from the group comprising polymers of olefines, cyclic olefines, acrylates, methacrylates, ethers, esters, urethanes, ether-esters, ether-urethanes, urethane acrylates, enols, including partially or perfluorinated analogons thereof, silicones, silicone acrylates and methacrylates, perfluorinated polymers selected from the group comprising perfluorinated polyacrylates, perfluorinated polymethacrylates, polyacrylates with perfluorinated side chains polymethacrylates with peifluorinated side chains or copolymers thereof; and
   the polymeric material of the transparent polymer waveguide is selected from the group comprising homocyclic heterocyclic aromatic polymers, including sulphur and bromium containing polymers, poly(pentabromophenyl methacrylate), Poly(vinylphenylsulfide), bisphenol-S based epoxides, and bisphenol-S based acrylates.

8. The optical sensor according to claim 1, wherein the upper surface of the polymer waveguide is covered with a thin noble metal layer.

9. System for detecting biological molecules, the system comprising:
   at least one optical sensor for use as biosensor, the optical sensor including:
      a transparent polymer substrate; and
      a thin transparent polymer waveguide coating at least a portion of the transparent polymer substrate, wherein the transparent polymer waveguide has a refractive index n of 1.4 to 1.79, the transparent polymer waveguide has a coupling grating recess structure for the coupling of light wave into the transparent polymer waveguide, a lower surface of the transparent polymer waveguide contacts the transparent polymer substrate, the transparent polymer substrate has a refractive index n of 1.29 to 1.69 and an upper surface of the polymer waveguide or optical sensor possess specific binding compounds to detect at least one specific chemical, wherein the lower surface of the waveguide possess at least one recess for enhancing the coupling of the light wave into the transparent polymer waveguide, wherein a depth of the at least one recess is less than the thickness of the the transparent polymer waveguide and wherein the transparent polymer substrate engages into the at least one recess;
   at least one light source; and
   one detector for the detection of the evanescently excited luminescence.

10. An evanescent field induced optical sensor for use as biosensor for detecting biological molecules, the optical sensor comprising:
   a transparent polymer substrate; and
   a thin transparent polymer waveguide coating at least a portion of the transparent polymer substrate, wherein the transparent polymer waveguide has a refractive index n of 1.4 to 1.79, the transparent polymer waveguide has a coupling grating recess structure for the coupling of light wave into the transparent polymer waveguide, a lower surface of the transparent polymer waveguide contacts the transparent polymer substrate, the transparent polymer substrate has a refractive index n of 1.29 to 1.69 and an upper surface of the polymer waveguide or optical sensor possess specific binding compounds to detect at least one specific chemical, wherein a thickness of the transparent polymer waveguide is selected so that X is in the range of 1 to 9, whereby d is calculated based on the equation:

$$X = \frac{d n_2 2\pi}{\lambda}$$

in which d is the thickness of the transparent polymer waveguide in nm, $n_2$ is the refractive index of the transparent polymer waveguide and $\lambda$ is the wavelength in nm.

11. The optical sensor according to claim 10, wherein X is in the range of 1.2 to 6.

12. The optical sensor according to claim 10, wherein X is in the range of 1.5 to 4.5.

13. The optical sensor according to claim 10, wherein the wavelength is in the range of 360 nm to 1000 nm.

14. The optical sensor according to claim 10, wherein the wavelength is in the range of 400 nm to 800 nm.

15. The optical sensor according to claim 10, wherein the wavelength is in the range of 550 nm to 700 nm.

16. The optical sensor according to claim 10, wherein the upper surface of the waveguide possess at least one recess for enhancing the coupling of the light wave into the transparent polymer waveguide, wherein a depth of the at least one recess is less than the thickness of the transparent polymer waveguide.

17. The optical sensor according to claim 16, wherein the lower surface of the waveguide possess at least one recess for enhancing the coupling of the light wave into the transparent polymer waveguide, wherein a depth of the at least one recess is less than the thickness of the transparent polymer waveguide and wherein the transparent polymer substrate engages into the at least one recess.

18. The optical sensor according to claim 17, wherein the at least one recess of the lower surface of the waveguide and the at least one recess of the upper surface of the waveguide are directly opposed.

19. Method of providing an optical sensor, the method comprising an act of:

forming at least one optical sensor for use as biosensor, the optical sensor including:

a transparent polymer substrate; and a thin transparent polymer waveguide coating at least a portion of the transparent polymer substrate, wherein the transparent polymer waveguide has a refractive index n of 1.4 to 1.79, the transparent polymer waveguide has a coupling grating recess structure for the coupling of light wave into the transparent polymer waveguide, a lower surface of the transparent polymer waveguide contacts the transparent polymer substrate, the transparent polymer substrate has a refractive index n of 1.29 to 1.69 and an upper surface of the polymer waveguide or optical sensor possess specific binding compounds to detect at least one specific chemical, wherein the lower surface of the waveguide possess at least one recess for enhancing the coupling of the light wave into the transparent polymer waveguide, wherein a depth of the at least one recess is less than the thickness of the transparent polymer waveguide and wherein the transparent polymer substrate engages into the at least one recess.

20. The method of providing an optical sensor according to claim 19, wherein at least one of the transparent polymer waveguide is spin-coated or printed on the upper surface of the transparent polymer substrate;

the transparent polymer substrate is molded or cast on a polymeric waveguide layer; and the grating structure is replicated from a micro structured mold.

21. The method according to claim 19, comprising an act of:

performing chemical analysis;

performing biological analysis, comprising analysis of biological fluids performing environmental analysis, comprising analysis of water, dissolved soil extracts or dissolved plant extracts;

performing dispersions or formulations analysis, comprising analysis in chemical production, in particular dye solutions or reaction solutions; or performing quality safeguarding analysis.

* * * * *